US00PP29895P2

(12) United States Plant Patent
Schroll

(10) Patent No.: US PP29,895 P2
(45) Date of Patent: Nov. 27, 2018

(54) ***HYDRANGEA* PLANT NAMED 'SCHROLL42-12-01'**

(50) Latin Name: *Hydrangea macrophylla*
Varietal Denomination: SCHROLL42-12-01

(71) Applicant: Soren Schroll, Odense SV (DK)

(72) Inventor: Soren Schroll, Odense SV (DK)

(73) Assignee: Schroll Management ApS, Odense SV (DK)

( * ) Notice: Subject to any disclaimer, the term of this patent is extended or adjusted under 35 U.S.C. 154(b) by 0 days.

(21) Appl. No.: 15/732,794

(22) Filed: Dec. 28, 2017

(51) Int. Cl.
*A01H 5/02* (2018.01)
*A01H 5/00* (2018.01)

(52) U.S. Cl.
USPC ..... Plt./250
CPC ..... *A01H 5/02* (2013.01); *A01H 5/00* (2013.01)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hydrangea* plant named 'SCHROLL42-12-01', characterized by its compact, upright and mounded plant habit; moderately vigorous to vigorous growth habit; freely branching habit and strong stems; dark green-colored leaves; large mophead-type inflorescences with white-colored sterile flowers with red purple-colored margins; long flowering period; and good postproduction quality and longevity.

2 Drawing Sheets

Botanical designation: *Hydrangea macrophylla.*
Cultivar denomination: 'SCHROLL42-12-01'.

BACKGROUND OF THE INVENTION

The present invention relates to a new and distinct cultivar of *Hydrangea* plant, botanically known as *Hydrangea macrophylla* and hereinafter referred to by the name 'SCHROLL42-12-01'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the spring of 2011 of a proprietary selection of *Hydrangea macrophylla* identified as code number 54-00, not patented, as the female, or seed, parent with a proprietary selection of *Hydrangea macrophylla* identified as code number 21-00, not patented, as the male, or pollen, parent. The new *Hydrangea* plant was discovered and selected by the Inventor in February, 2013 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2013 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL42-12-01'. These characteristics in combination distinguish 'SCHROLL42-12-01' as a new and distinct *Hydrangea* plant:

1. Compact, upright and mounded plant habit.
2. Moderately vigorous to vigorous growth habit.
3. Freely branching habit and strong stems.
4. Dark green-colored leaves.
5. Large mophead-type inflorescences with white-colored sterile flowers with red purple-colored margins.
6. Long flowering period.
7. Good postproduction quality and longevity.

Plants of the new *Hydrangea* differ primarily from plants of the female parent selection in the following characteristics:

1. Leaves of plants of the new *Hydrangea* are darker green in color than leaves of plants of the female parent selection.
2. Plants of the new *Hydrangea* and the female parent selection differ in sterile flower color as sterile flowers of plants of the female parent selection are light pink in color.
3. Plants of the new *Hydrangea* force faster than plants of the female parent selection.

Plants of the new *Hydrangea* differ primarily from plants of the male parent selection in the following characteristics:

1. Plants of the new *Hydrangea* are more compact than plants of the male parent selection.
2. Leaves of plants of the new *Hydrangea* are darker green in color than leaves of plants of the male parent selection.

3. Plants of the new *Hydrangea* and the male parent selection differ in sterile flower color as sterile flowers of plants of the male parent selection are white in color with pink-colored margins.
4. Plants of the new *Hydrangea* force faster than plants of the male parent selection.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the new *Hydrangea* are more compact than and not as vigorous as plants of 'H213901'.
2. Leaves of plants of the new *Hydrangea* are darker green in color than leaves of plants of 'H213901'.
3. Inflorescences of plants of the new *Hydrangea* have more sterile and fewer fertile flowers than inflorescences of plants of 'H213901'.
4. Plants of the new *Hydrangea* and 'H213901' differ in sterile flower color as sterile flowers of plants of 'H213901' are dark red purple in color.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* and 'H213906' differ in sterile flower color as sterile flowers of plants of 'H213906' are dark pink in color.
2. Plants of the new *Hydrangea* force faster than plants of 'H213906'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SCHROLL42-12-01' grown in a container.

The photograph on the second sheet is a close-up view of a typical developed inflorescence of 'SCHROLL42-12-01'.

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched one time and were one year old when the photographs and description were taken. During the production of the plants, day temperatures ranged from 15° C. to 25° C., night temperatures ranged from 10° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLL42-12-01'.

Parentage:

*Female, or seed, parent*.—Proprietary selection of *Hydrangea macrophylla* identified as code number 54-00, not patented.

*Male, or pollen, parent*.—Proprietary selection of *Hydrangea macrophylla* identified as code number 21-00, not patented.

Propagation:

*Type cutting*.—By softwood cuttings.

*Time to initiate roots, summer*.—About ten days at temperatures about 20° C.

*Time to initiate roots, winter*.—About two weeks at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Low branching; sparse.

Plant description:

*Plant and growth habit*.—Perennial subshrub; compact, upright and mounded plant habit; broadly inverted triangle; freely branching habit with about six to seven lateral branches developing per plant; strong lateral branches; moderately vigorous to vigorous growth habit.

*Plant height*.—About 30 cm.

*Plant diameter or area of spread*.—About 30 cm to 35 cm.

*Lateral branches*.—Length: About 20 cm to 25 cm. Diameter: About 5 mm to 6 mm. Internode length: About 3 cm to 4 cm. Strength: Strong. Texture: Smooth, glabrous. Color, developing: Close to 147C. Color, developed: Close to 144B. Color, lenticels: Close to N199B.

Leaf description:

*Arrangement*.—Opposite, decussate; simple.

*Length*.—About 8 cm to 10 cm.

*Width*.—About 7 cm to 8 cm.

*Shape*.—Ovate to elliptic.

*Apex*.—Apiculate.

*Base*.—Obtuse to rounded.

*Margin*.—Entire to slightly serrate.

*Texture and luster, upper surface*.—Smooth to rugose, glabrous; semi-glossy.

*Texture and luster, lower surface*.—Rugose, glabrous; prominent venation; matte.

*Venation pattern*.—Pinnate, reticulate.

*Color*.—Developing leaves, upper surface: Close to N186A. Developing leaves, lower surface: Close to N186C. Fully expanded leaves, upper surface: Close to N137A; towards the margins, close to N186A; venation, close to 145A to 145B. Fully expanded leaves, lower surface: Close 146A to 146B; towards the margins, close to 187A; venation, close to 145B to 145C.

*Petioles*.—Length: About 2 cm. Diameter: About 4 mm to 5 mm. Strength: Strong. Texture, upper and lower surfaces: Smooth, glabrous. Color, upper and lower surfaces: Close to 144C.

Inflorescence & flower description:

*Flower type and habit*.—Showy single sterile and inconspicuous single fertile flowers arranged on terminal mophead-type panicles; panicles hemispherical to flattened globular in overall shape; fertile and sterile flowers face upright to outwardly; early flowering habit, plants begin flowering about seven to eight weeks after forcing period.

*Natural flowering season*.—Long flowering period, continuous flowering from June throughout the summer in Northern Europe.

*Flower longevity, fertile flowers*.—Flowers last up to three weeks on the plant; fertile flowers not persistent.

*Flower longevity, sterile flowers*.—Flowers last about four months on the plant; sterile flowers persistent.

*Quantity of flowers*.—Freely flowering habit with less than 20 fertile flowers and about 150 sterile flowers per panicle.

*Fragrance*.—None detected.

*Panicle height*.—About 6 cm to 7 cm.

*Panicle diameter*.—About 15 cm.

*Flower diameter, fertile flowers*.—About 2 mm.

*Flower depth (height), fertile flowers*.—About 2 mm.

*Flower diameter, sterile flowers*.—About 3.5 cm to 4 cm.

*Flower depth (height), sterile flowers*.—About 1 cm.

*Flower shape, fertile flowers*.—Spherical.

*Flower shape, sterile flowers*.—Deltoid.

*Flower buds, fertile flowers*.—Length: About 2 mm. Diameter: About 2 mm. Shape: Spherical. Color: Close to 68A to 68B.

*Flower buds, sterile flowers*.—Length: About 2 mm to 3 mm. Diameter: About 1 mm to 2 mm. Shape: Spherical. Color: Close to 144C; distally, close to 71A.

*Petals, fertile flowers*.—Quantity and arrangement: Five in a single whorl. Length: About 3 mm to 4 mm. Width: About 2 mm. Shape: Ovate. Apex: Acute. Base: Rounded. Margin: Entire. Texture, upper and lower surfaces: Smooth, glabrous. Color: When opening, upper and lower surfaces: Close to 145A. Fully opened, upper and lower surfaces: Close to 71C to 71D.

*Petals, sterile flowers*.—Quantity and arrangement: Four or five in a single whorl. Length: About 2.5 mm. Width: About 1.2 mm to 1.5 mm. Shape: Roughly ovate. Apex: Broadly acute. Base: Rounded. Margin: Entire. Texture, upper and lower surfaces: Smooth, glabrous. Color: When opening, upper and lower surfaces: Close to 68A to 68B. Fully opened, upper and lower surfaces: Close to 68B; color does not change with development.

*Sepals, fertile flowers*.—Quantity and arrangement: Five in a single whorl; imbricate. Length: About 4 mm to 5 mm. Width: About 2 mm to 3 mm. Shape: Ovate. Apex: Acute. Base: Rounded. Margin: Entire. Texture, upper surface: Fine pubescence. Texture, lower surface: Smooth, glabrous. Color: When opening and fully opened, upper surface: Close to 144D. When opening and fully opened, lower surface: Close to 144D.

*Sepals, sterile flowers*.—Quantity and arrangement: Four to six in a single whorl; imbricate. Length: About 2 cm to 2.5 cm. Width: About 2 cm to 2.5 cm. Shape: Cordate. Apex: Subacute. Base: Truncated, slightly rounded. Margin: Entire; undulate. Texture, upper surface: Slightly rippled, glabrous. Texture, lower surface: Rippled, glabrous. Color: When opening, upper surface: Close to 145B; towards the margins, close to 64A. When opening, lower surface: Close to 145A to 145B; towards the margins, close to 64A to 64B. Fully opened, upper surface: Close to 157C; towards the margins, close to 64B; white colored areas becoming closer to 144D with development. Fully opened, lower surface: Close to 157C; towards the margins, close to 64B; white colored areas becoming closer to 144C with development.

*Pedicels, fertile flowers*.—Length: About 6 mm to 7 mm. Diameter: About 1 mm. Strength: Strong. Aspect: Upright to outwardly. Texture: Fine pubescence. Color: Close to 144A.

*Pedicels, sterile flowers*.—Length: About 2 cm. Diameter: About 2 mm to 2.5 mm. Strength: Strong. Aspect: Mostly upright. Texture: Smooth, glabrous. Color: Close to 145D.

*Reproductive organs, fertile flowers*.—Stamens: Quantity per flower: About eight. Filament length: About 2 mm. Filament color: Close to 67C. Anther length: About 1 mm. Anther shape: Reniform, elongated. Anther color: Close to 11D; spots, close to 67C. Pollen amount: Abundant. Pollen color: Close to 155D. Pistils: Pistil quantity per flower: About three. Pistil length: About 1 mm to 1.5 mm. Stigma shape: Oval to almost round. Stigma color: Close to 64D. Style length: About 1 mm to 1.5 mm. Style color: Close to 68A. Ovary color: Close to 68A.

*Reproductive organs, sterile flowers*.—Stamens: Quantity per flower: About eight to ten. Filament length: About 1.2 mm. Filament color: Close to 62A. Anther length: About 0.5 mm. Anther shape: Elliptical, elongated. Anther color: Close to 11D. Pollen amount: Moderate. Pollen color: Close to 19D. Pistils: Pistil quantity per flower: About three. Pistil length: About 1 mm. Stigma shape: Roughly oval. Stigma color: Close to 62A. Style length: About 1.2 mm. to 1.3 mm. Style color: Close to N57D. Ovary color: Close to N57D.

*Seeds*.—Quantity: Between 30 to 100. Length: About 0.5 mm. Diameter: About 0.2 mm. Color: Close to 199B.

Pathogen & pest resistance: Plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 4° C. to 35° C.

It is claimed:

1. A new and distinct *Hydrangea* plant named 'SCHROLL42-12-01' as illustrated and described.

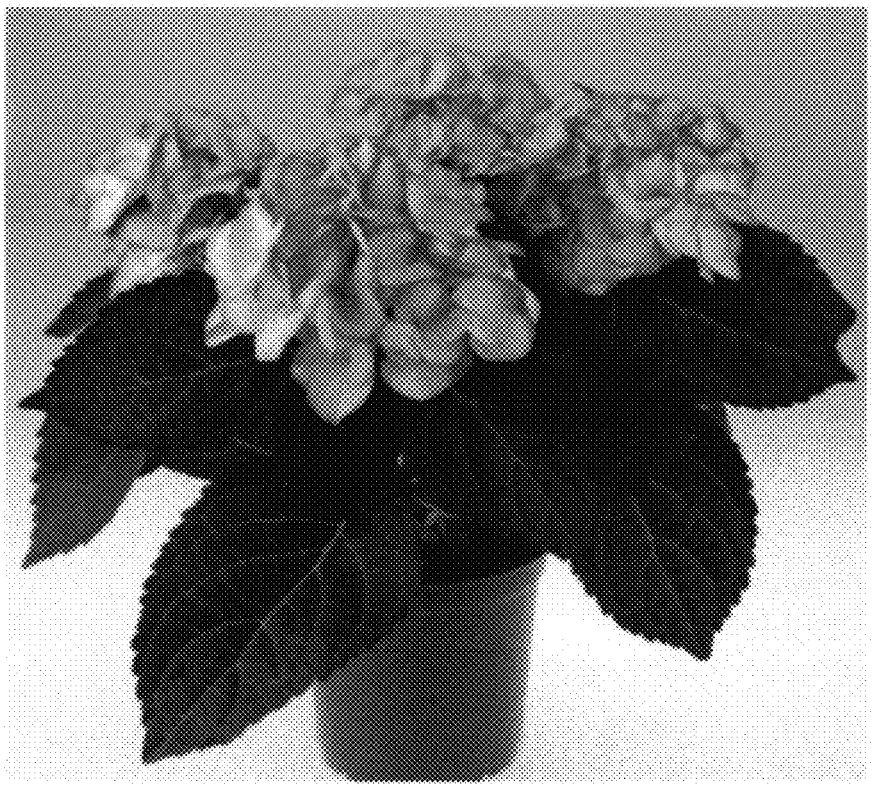

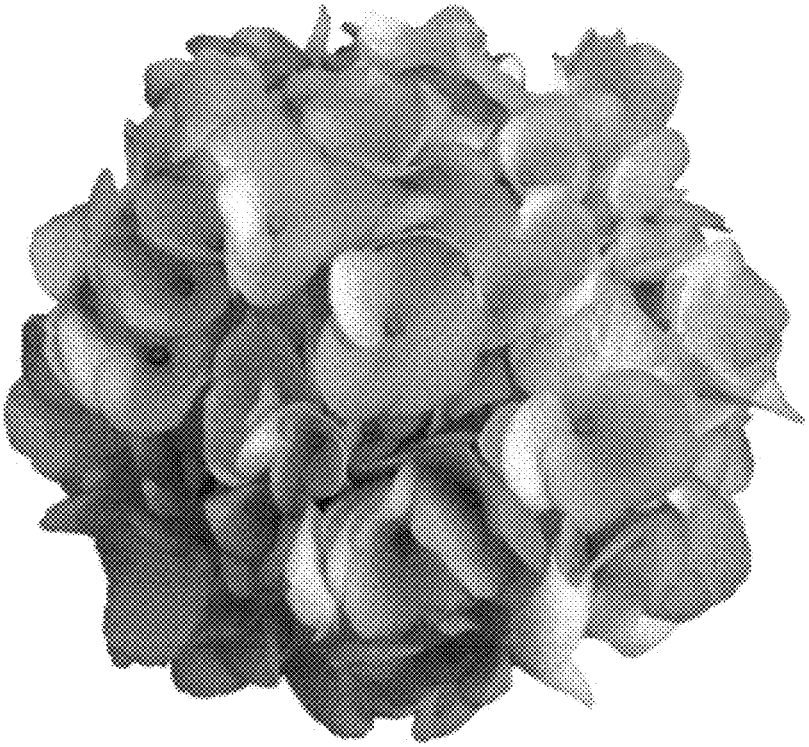

* * * * *